United States Patent [19]

Braish

[11] Patent Number: 5,298,629
[45] Date of Patent: Mar. 29, 1994

[54] INTERMEDIATES IN THE SYNTHESIS OF QUINOLINE ANTIBIOTICS

[75] Inventor: Tamin F. Braish, Ledyard, Conn.

[73] Assignee: Pfizer Inc., New York, N.Y.

[21] Appl. No.: 101,879

[22] Filed: Aug. 4, 1993

Related U.S. Application Data

[63] Continuation-in-part of Ser. No. 844,367, Mar. 2, 1992, Pat. No. 5,256,791.

[51] Int. Cl.$^5$ .............................................. C07D 209/52
[52] U.S. Cl. ..................................................... 548/452
[58] Field of Search ........................................ 548/452

[56] References Cited

U.S. PATENT DOCUMENTS 5,196,548  3/1993  Braish et al. ............... 548/453
5,200,527  4/1993  Griffiths et al. ............ 548/452

*Primary Examiner*—David B. Springer
*Attorney, Agent, or Firm*—Peter C. Richardson; Paul H. Ginsburg

[57] ABSTRACT

This invention relates to compounds of the formulae

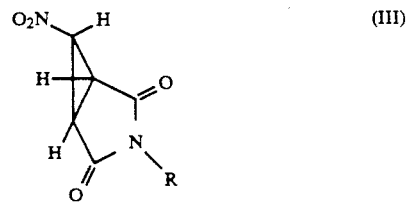

and

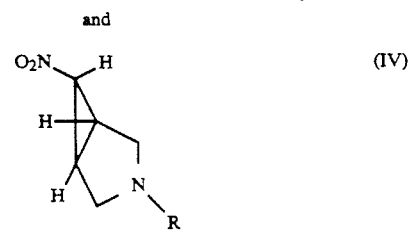

wherein R and X are defined as below. These compounds are useful as intermediates in the syntheses of azabicyclo quinoline carboxylic acids having antibacterial activity.

7 Claims, No Drawings

INTERMEDIATES IN THE SYNTHESIS OF QUINOLINE ANTIBIOTICS

BACKGROUND OF THE INVENTION

This patent application is a continuation in part of U.S. application Ser. No. 07/844,367, which was filed on Mar. 2, 1992, now U.S. Pat. No. 5,256,791.

This invention relates to novel intermediates in the synthesis of the quinoline antibiotic 7-(1α,5α,6α)-(6-amino-3-azabicyclo[3.1.0]hex-3-yl)-1-(2,4-difluorophenyl)-6-fluoro-1,4-dihydro-4-oxo-1,8-naphthyridine-3-carboxylic acid and related antibiotic compounds. The quinoline antibiotic 7-(1α,5α,6α)-(6-amino-3-azabicyclo[3.1.0]hex-3-yl)-1-(2,4-difluorophenyl)-6-fluoro-1,4-dihydro-4-oxo-1,8-naphthyridine-3-carboxylic acid has the chemical formula

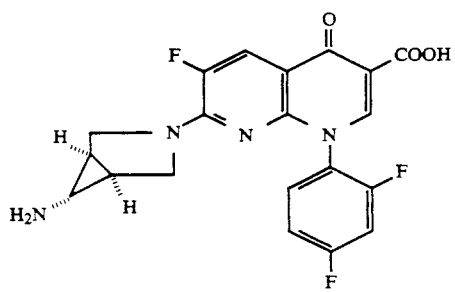

(I)

This compound and related azabicyclo quinoline carboxylic acid that exhibit antibacterial activity are referred to in U.S. patent application Ser. No. 07/551,212, filed on Jul. 11, 1990 and World Patent Application WO 91/02526, filed on Aug. 16, 1989 and published on Mar. 7, 1991. Both of the foregoing applications are assigned in common with the present application and are incorporated herein by reference in their entirety.

The novel compounds of this invention may be used to prepare compounds of the formula

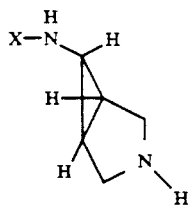

(VII)

which are intermediates in the synthesis of the quinoline antibiotic of the formula I and the azabicyclo quinoline carboxylic acid antibiotics referred to above. The methods by which compounds of the formula VII may be converted into such antibiotic compounds are set forth in detail in U.S. patent application Ser. No. 07/551,212 and World Patent Application WO 91/02526.

SUMMARY OF THE INVENTION

This invention relates to compounds having the formula

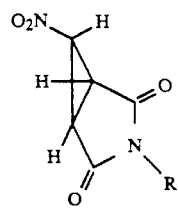

(III)

or

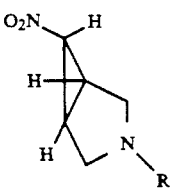

(IV)

wherein R is ($C_1$-$C_6$) straight or branched alkyl, ($C_3$-$C_6$)cycloalkyl, benzyl, diphenylmethyl or triphenylmethyl, wherein the phenyl moieties of said benzyl, diphenylmethyl and triphenylmethyl (also referred to as "trityl") groups may be substituted, optionally, with one or more substituents, preferably with from zero to two substituents independently selected from halo (e.g., chloro, fluoro, bromo or iodo), nitro, ($C_1$-$C_6$) alkyl, ($C_1$-$C_6$) alkoxy, amino and trifluoromethyl.

Preferred compounds of the formulae III and IV are those wherein R is benzyl or trityl.

DETAILED DESCRIPTION OF THE INVENTION

Processes for preparing the compounds of the present invention and compounds of the formula VII are illustrated in the following reaction scheme. Except where otherwise indicated, in the reaction scheme and discussion that follow, formulas I, II, III and IV, and substituents R and X are defined as above.

SCHEME

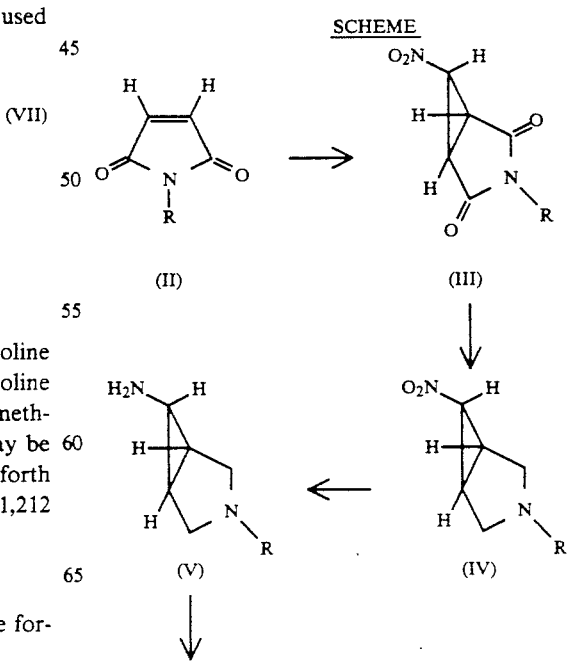

-continued
SCHEME

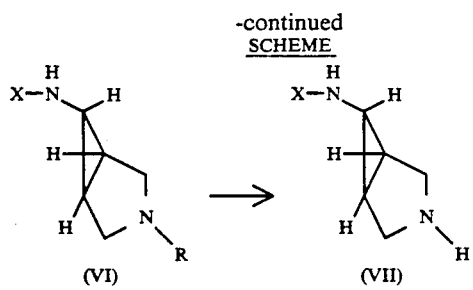

The above reaction scheme illustrates the preparation of compounds of the formula VII, which are useful intermediates in the synthesis of the quinoline antibiotics referred to above.

Referring to the scheme, compounds of the formula II wherein R is benzyl, ($C_1$–$C_6$) straight or branched alkyl or ($C_3$–$C_8$)cycloalkyl are commercially available or known in the art. Compounds of the formula II wherein R is diphenylmethyl or triphenylmethyl may be prepared by reacting the compound

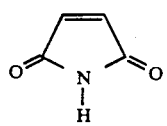

with diphenylmethyl chloride or triphenylmethyl chloride, respectively, in the presence of a an organic base such as triethylamine. This reaction is usually carried out in an inert solvent such as tetrahydrofuran (THF), methylene chloride ($CH_2Cl_2$) or chloroform ($CHCl_3$), preferably chloroform, at a temperature from about −20° C. to about 80° C., preferably about 25° C.

Reaction of a compound having formula II with a halonitromethane, preferably chloronitromethane ($ClCH_2NO_2$) or bromonitromethane ($BrCH_2NO_2$), in the presence of a base yields the corresponding compound of the formula III. This reaction is generally conducted in an inert, polar, aprotic solvent such as dimethylformamide (DMF), dimethylsulfoxide (DMSO) or dimethylacetamide (DMAC), an inert etheral solvent such as ethyl ether, glyme or tetrahydrofuran (THF), or another inert solvent such as benzene, toluene or a chlorinated benzene or toluene. Toluene is preferred. Suitable reaction temperatures range from about −78° C. to about 80° C., with about 0° C. being preferred. It is preferable to add the base last. Examples of appropriate bases include carbonate bases such as potassium or sodium carbonate, phosphrine amide bases such as 2-tert-butylimino-2-diethylamino-1,3-dimethyl-perhydro-1,3,2-diaza-phosphorine, and amine bases such as triethylamine, guanidine, diisopropylethylamine, tetramethyl guanidine, 1,8-diazaobicyclo-[5.4.0]undec-7-ene (DBU) and 1,5-diazaobicyclo-[4.3.0]non-5-ene (DBN). It is advantageous to use an amine base and, most preferably, to use DBU.

Reduction of the compound of formula III so formed yields the corresponding compound of formula IV. Appropriate reducing agents include borane/dimethylsulfide, borane/THF, sodium borohydride and a borontrifluoride•etherate mixture. The preferred reducing agent is borane/THF. The reduction is typically carried out at temperatures ranging from about 20° C. to about 90° C., in an inert etheral solvent such as glyme, diglyme, diethylether, diisopropyl ether or THF. It is preferably carried out at about 66° C. in THF.

The resulting compound of the formula IV may be converted into the corresponding amine of formula V by treating it with a metal and an inorganic acid. The preferred metal is zinc. Suitable inorganic acids include hydrochloric acid, sulfuric acid. Hydrochloric acid is preferred. This reaction is generally conducted in a lower alcohol solvent such as ethanol, methanol, 1-propanol or 2-propanol, preferably ethanol, at a temperature from about 0° C. to about 80° C., preferably at about 25° C.

The corresponding compound of formula VI, wherein X is a nitrogen protecting group, is then formed by adding a suitable nitrogen protecting group to the unsubstituted amino nitrogen of the compound of formula V. Several well known nitrogen protecting groups can be used. Such groups include ($C_2$–$C_6$) alkoxycarbonyl, optionally substituted benzyloxycarbonyl, aryloxycarbonyl, silyl, trityl, vinyloxycarbonyl, O-nitrophenylsulfonyl, acetate, p-toluenesulfonyl, and benzyl. It is advantageous to use di-t-butyldicarbonate or 2-t-butoxycarbonyloxyimino-2-phenylacetonitrile. The addition of the nitrogen protecting group is usually carried out in a chlorinated hydrocarbon solvent such as methylene chloride or 1,2-dichloroethane, or an ethereal solvent such as glyme, diglyme or THF, in the presence or absence of a catalytic amount of an amine base such as triethylamine, diisopropylethylamine or pyridine, preferably triethylamine, at a temperature from about 0° C. to about 50° C., preferably at about 25° C.

When R is benzyl, diphenylmethyl or triphenylmethyl, the hydrogenolytic removal of the R group from the compound of formula VI formed in the foregoing step yields the desired compound of formula VII. This is generally accomplished by reacting the compound of formula VI, wherein R is benzyl, diphenylmethyl or triphenylmethyl, with hydrogen gas at a pressure from about 0 psi to about 2000 psi, preferably about 50 psi, in the presence of a noble catalyst such as palladium, platinum or rhodium. Palladium on carbon or palladium hydroxide on carbon is preferred. The temperature may range from about 20° C. to about 80° C., and is preferably about 25° C. The solvent is usually a lower alcohol and is preferably methanol.

When R is ($C_1$–$C_6$) alkyl or ($C_3$–$C_6$) cycloalkyl, the R group may be removed by reaction with α-chloroethylchloroformate (ACE-Cl). (See Olefson et al., *J. Org. Chem.*, 49, 2081-2 (1984) and Olefson et al., *Pure & Appl. Chem.*, 60(11), 1715-24 (1988)).

The procedures by which compounds of the formula VII may be used to prepare the quinoline antibiotic having formula 1 and related azabicyclo quinoline carboxylic acid antibiotics are set forth in U.S. patent application Ser. No. 07/551,212, filed on Jul. 11, 1990 and World Patent Application, WO 91/02526, filed on Aug. 16, 1989 and published on Mar. 7, 1991, both on which are incorporated herein by reference in their entirety.

The antibacterial compound having formula I and the related azabicyclo quinoline carboxylic acid antibiotics that can be synthesized using the methods and compounds of this invention are useful in the treatment of animals, including humans, having bacterial infections. They are useful in treating bacterial infections of broad spectrum, particularly in treating gram-positive bacterial strains.

U.S. patent application Ser. No. 07/551,212 and World Patent Application WO 91/02526 set forth in detail the appropriate dosage ranges and methods of administration of such antibiotic compounds. These references also set forth a method by which the antibacterial activity of such compounds may be determined.

The following examples illustrate the methods and compounds of the present invention. It will be understood, however, that the invention is not limited to the specific details of these examples.

EXAMPLE 1

1α, 5α, 6α-3-Benzyl-6-nitro-2,4-dioxo-3-azabicyclo[3.1.0]hexane

To N-benzylmaleimide (24.3 g, 130 mmol) and bromonitromethane (18.2 ml, 260 mmol) was added 250 ml of toluene and the mixture was cooled to 0° C. While stirring vigourously with an overhead stirrer, 1,8-diazabicyclo[5.4.0]undec-7-ene (DBU) (58 ml, 390 mmol) diluted with 200 ml of toluene was added dropwise over a period of 30 min. The reaction was allowed to stir for 2 additional hours at room temperature. The toluene layer was decanted and washed with (2×100 ml) 0.1M HCl solution and dried over magnesium sulfate (MgSO$_4$). Evaporation of the solvent provided 5.4 g of the product which represents a 17% yield. M.P.=114°–115.5° C. $^1$H NMR (CDCl$_3$): 7.31 (m, 5H, aromatics), 4.54 (s, 2H, benzylic), 4.47 (t, 1H, alpha to nitro), 3.35 (d, 2H, 3-ring).

EXAMPLE 2

1α, 5α, 6α-3-Benzyl-6-nitro-3-azabicyclo[3.1.0]hexane

To the 1α, 5α, 6α-3-benzyl-6-nitro-2,4-dioxo-3-azabicyclo[3.1.0]hexane (2 g, 8.1 mmol) from Example 1 in 20 ml of THF was added borane•THF complex (32.4 ml of 1M solution in THF, 32.4 mmol) and the mixture was heated to reflux for 3 hours. The reaction was cooled to room temperature and 10 ml of methanol was carefully added. Heating to reflux was then resumed for 15 min. The solvent was then evaporated and the residual oil was dissolved in 200 ml of CH$_2$Cl$_2$ and washed with water (3×100). The organic layer was dried over MgSO$_4$ and evaporated to provide 1.5 g of the product (light oil) which represents a 90% yield. $^1$H NMR (CDCl$_3$): 7.35–7.19 (m, 5H, aromatics), 4.63 (t, 1H, alpha to nitro), 3.59 (s, 2H, benzylic), 3.14 (m, 2H, 5-ring), 2.49 (m, 2H, 5-ring), 2.51 (m, 2H, 3-ring).

EXAMPLE 3

1α, 5α, 6α-3-Benzyl-6-amino-3-azabicyclo[-3.1.0]hexane

To the 1α, 5α, 6α-3-benzyl-6-nitro-3-azabicyclo[3.1.0]hexane (6 g, 27.5 mmol) from Example 2 in 50 ml of ethanol was added zinc dust (18.0 g, 275 mmol). To that was added 150 ml of 1M HCl solution such a rate that the temperature of the reaction never exceeded 40° C. (1 hour). The reaction was allowed to stir at room temperature for 3 hours after which it was filtered through Celite ®. The solvents were then evaporated and the thick white residue was digested with 500 ml of 1M NaOH solution for 3 hours. The mixture was extracted with (2×300 ml) CH$_2$Cl$_2$ and the combined organic layers were washed with brine (3×100) and dried over MgSO$_4$. Evaporation of the solvent provided 4.06 g of the product which represents a 79% yield. $^1$H NMR (CDCl$_3$): 7.35–7.20 (m, 5H, aromatics), 4.62 (broad singlet, 1H, alpha to nitro), 3.60 (s, 2H, benzylic), 3.14 (m, 2H, 5-ring), 2.52 (m, 2H, 5-ring and m, 2H, cyclopropyl).

EXAMPLE 4

1α, 5α, 6α-3-Benzyl-6-[(t-butyl formyl)amino]-3-azabicyclo[3.1.0]hexane

To the 1α, 5α, 6α-3-benzyl-6-amino-3-azabicyclo[3.1.0]hexane from Example 3 (3.75 g, 19.9 mmol) in 50 ml of THF was added di-t-butyl dicarbonate (4.78 g, 21.9 mmol) and triethylamine (0.28 ml, 1.99 mmol), and the mixture was allowed to stir for 4 hours. The solvent was then evaporated and 75 ml of methylene chloride (CH$_2$Cl$_2$) was added. The mixture was washed with 20 ml of water and dried over MgSO$_4$. The solvent was evaporated and replaced with 100 ml of hexane. The mixture was heated until all the solids dissolved and 2.5 g of activated charcoal was added and heating was continued for 5 min. The carbon was filtered. Upon cooling the reaction mixture, a solid formed which was filtered and dried in air. The product weighed 5.1 g which represents an 89% yield. M.P.=131°–132° C. (white needles). $^1$H NMR (CDCl$_3$): 7.24 (m, 5H, aromatics), 3.54 (s, 2H, benzylic), 3.06 (m, 2H, 5-ring), 2.91 (broad, 1H, alpha to amide), 2.43 (m, 2H, 5-ring), 1.52 (m, 2H, 3-ring).

EXAMPLE 5

1α, 5α, 6α-[(t-Butyl formyl)amino]-3-azabicyclo[3.1.0]hexane

To 1α, 5α, 6α-3-benzyl-6-[(t-butyl formyl)amino]-3-azabicyclo[3.1.0]hexane from Example 4 (2.0 g, 6.94 mmol) in 50 ml of methanol was added palladium hydroxide on carbon (Pd(OH)$_2$/C) (50% wet) (1.0 g, 50% by weight). The mixture was hydrogenated at 50 PSI for 6 hours and was then filtered through Celite ® and the solvent was evaporated to provide 1.36 g of the product in 99% yield. $^1$H NMR (CDCl$_3$): 3.22–2.95 (m, 4H, 5-ring), 2.61 (broad, 1H, amide), 2.32 (m, 1H, alpha to amide), 1.63 (m, 2H, 3-ring), 1.45 (s, 9H, butyl).

EXAMPLE 6

N-Tritylmaleimide

Maleimide (20.0 g, 206 mmol) and trityl chloride (57.4 g, 206 mmol) were mixed together in 200 ml of chloroform and triethylamine (31.3, 309 mmol) was added dropwise to the reaction over a period of 20 minutes. After stirring for one hour at room temperature, the reaction was washed with 10% aqueous hydrogen chloride (HCl) solution and dried over magnesium sulfate (MgSO$_4$). The crude product was slurried in 20 ml of ethylacetate. A total of 18.4 g of a solid material was filtered and dried (60% yield). $^1$H NMR (CDCl$_3$): 7.31 (m, 15H, aromatics), 6.25 (s, 2H, vinyl).

EXAMPLE 7

1α, 5α, 6β-3-trityl-6-nitro-2,4-dioxo-3-azabicyclo[3.1.0]hexane

To N-tritylmaleimide (1.90, 5.6 mmol) in 60 ml of toluene and 20 ml of tetrahydrofuran (THF) was added bromonitromethane (1.57 g, 11.2 mmol) and the mixture was cooled to 0° C. To that DBU (2.55 g, 16.8 mmol) in 10 ml of toluene was added dropwise over a period of 30 minutes. The reaction was allowed to stir for an additional 30 minutes and was washed with cold 10% HCl solution and dried over MgSO$_4$. Evaporation of the solvent provided 700 mg of product (32% yield). $^1$H NMR (CDCl$_3$): 7.0–7.5 (m, 15H, aromatics), 4.90 (t, 1H, alpha to nitro), 3.31 (d, 2H).

EXAMPLE 8

1α, 5α, 6β-3-trityl-6-nitro-3-azabicyclo[3.1.0]hexane

The 1α, 5α, 6β-3-trityl-6-nitro-2,4-dioxo-3-azabicyclo[3.1.0]hexane (700 mg, 1.76 mmol) dissolved in 35 ml of THF was added to a solution of sodium borohydride (200 mg, 5.28 mmol) and boron trifluoride etherate (1.0 g, 7.03 mol) at 0° C. The mixture was allowed to stir for 16 hours at room temperature and the reaction was quenched with 10 ml of methanol. The reaction was heated to reflux for 15 minutes and cooled. The solvents were evaporated and the residual oil was partitioned between 100 ml of methylene chloride (CH$_2$Cl$_2$) and 30 ml of water. The organic layer was dried and evaporated and the residual oil was used as is in the next step.

EXAMPLE 9

1α, 5α, 6β-3-trityl-6-amino-3-azabicyclo[3.1.0]hexane

The crude oil from the previous reaction (1α, 5α, 6β-3-trityl-6-nitro-3-azabicyclo[3.1.0]hexane) was dissolved in 25 ml of ethanol and to it was added zinc dust (1.8 g, 27.5 mmol). Then, 15 ml of 1M HCl solution was added at such a rate that the temperature of the reaction never exceeded 40° (1 hour). The reaction was allowed to stir at room temperature for 3 hours, after which it was filtered through Celite ®. The solvents were then evaporated and the thick white residue was digested with 100 ml of 1M sodium hydroxide (NaOH) solution for 3 hours. The mixture was extracted with (2×100 ml) CH$_2$Cl$_2$ and the combined organic layers were washed with brine (100 ml) and dried over MgSO$_4$. Evaporation of the solvent provided 462 mg of the product which represents an 80% yield. $^1$H NMR (CDCl$_3$): 7.35–7.20 (m, 15H, aromatics), 4.58 (broad singlet, 1H, alpha to nitro), 3.65 (s, 2H, benzylic), 3.0 (m, 2H, 5-ring), 2.52 (m, 2H, 5-ring and m, 2H, cyclopropyl).

EXAMPLE 10

1α, 5α, 6β-3-trityl-6-acetylamino-3-azabicyclo[3.1.0]hexane

To 1α, 5α, 6β-3-trityl-6-amino-3-azabicyclo[3.1.0]hexane (300 mg, 0.91 mmol) in 15 ml of CH$_2$Cl$_2$ was added acetic anhydride (93.3 mg, 0.91 mmol) and triethylamine (101.8 mg, 1.0 mmol). The mixture was allowed to stir at room temperature for 6 hours. The reaction was diluted with 20 ml of CH$_2$Cl$_2$ and washed with 10 ml of water. The organic layer was dried and evaporated to give 305 mg of the desired acetate (91% yield). $^1$H NMR (CDCl$_3$): 7.0–7.5 (m, 15H, aromatics), 3.06 (m, 2H, 5-ring), 2.8 (broad, 1H, alpha to amide), 2.6 (s, 3H, acetate), 2.3 (m, 2H, 5-ring), 1.52 (m, 2H, 3-ring).

EXAMPLE 11

1α, 5α, 6β-6-acetylamino-3-azabicyclo[3.1.0]hexane

To the 1α, 5α, 6β-3-trityl-6-acetylamino-3-azabicyclo[3.1.0]hexane (305 mg, 0.82 mmol) was added 15 ml of acetic acid and the mixture was hydrogenated in the presence of palladium on carbon at 60° C. for 16 hours. The solvent was evaporated, 30 ml of water was added and the aqueous layer was extracted twice with 20 ml of CH$_2$Cl$_2$ to remove the triphenylmethane. The pH of the aqueous layer was adjusted to 12. The extractions with CH$_2$Cl$_2$ provided 80 mg of the desired product after evaporation of the solvent (70%).

I claim:

1. A compound having the formula

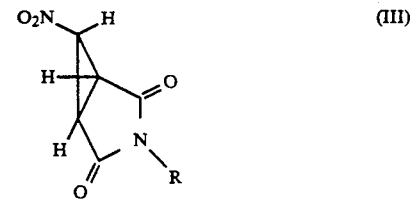

(III)

or

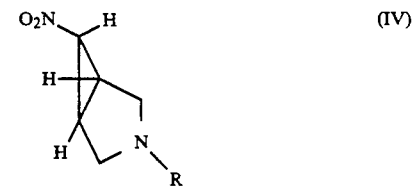

(IV)

wherein R is (C$_1$–C$_6$) straight or branched alkyl, benzyl, diphenylmethyl or triphenylmethyl, and wherein the phenyl moieties of said benzyl, diphenylmethyl and triphenylmethyl groups may be substituted, optionally, with one or more substituents independently selected from halo, nitro, (C$_1$–C$_6$) alkyl, (C$_1$–C$_6$) alkoxy, amino and trifluoromethyl.

2. A compound according to claim 1 having the formula III.

3. A compound according to claim 2 wherein R is benzyl.

4. A compound according to claim 2 wherein R is trityl.

5. A compound according to claim 1 having the formula IV.

6. A compound according to claim 5 wherein R is benzyl.

7. A compound according to claim 5 wherein R is trityl.

* * * * *